US008416984B2

(12) United States Patent
Liang et al.

(10) Patent No.: US 8,416,984 B2
(45) Date of Patent: Apr. 9, 2013

(54) AUTOMATIC TOOTH CHARTING USING DIGITAL IMAGES

(75) Inventors: Rongguang Liang, Penfield, NY (US); Jean Marc Inglese, Bussy Saint Georges (FR); Edward R. Shellard, Atlanta, GA (US); Larry A. Greenspan, Sparks, MD (US); Mark Woodman, Biggleswade (GB); Steve Mclaughlin, Biggleswade (GB)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 13/010,031

(22) Filed: Jan. 20, 2011

(65) Prior Publication Data

US 2012/0189182 A1 Jul. 26, 2012

(51) Int. Cl.
*G06K 9/00* (2006.01)
(52) U.S. Cl.
USPC .......................................... 382/100; 382/154
(58) Field of Classification Search .................... 382/154
See application file for complete search history.

(56) References Cited

U.S. PATENT DOCUMENTS

| | | | |
|---|---|---|---|
| 6,532,299 B1 * | 3/2003 | Sachdeva et al. | 382/128 |
| 7,010,153 B2 | 3/2006 | Zimmermann | |
| 7,596,253 B2 | 9/2009 | Wong et al. | |
| 2002/0168602 A1 | 11/2002 | Taub et al. | |
| 2002/0178032 A1 | 11/2002 | Benn et al. | |
| 2004/0038184 A1 * | 2/2004 | Adachi et al. | 433/215 |
| 2004/0049956 A1 * | 3/2004 | Li | 40/124.06 |
| 2006/0069591 A1 * | 3/2006 | Razzano | 705/2 |
| 2006/0270935 A1 * | 11/2006 | Ariff et al. | 600/437 |
| 2006/0285636 A1 | 12/2006 | Razzano | |

OTHER PUBLICATIONS

Earley, Edward T., DVM, "Computerized Dental Charting", AAEP (American Association of Equine Practitioners) Focus Meeting 2006, International Veterinary Information Service, Filename: earley1.pdf currently available at the http:// address: www.ivis.org/proceedings/aaepfocus/2006/. 16 pages.
"Dental Charting" training document, National Examining Board for Dental Nurses, National Certificate Examination, NEBDN—England and Wales, Apr. 2009. pp. 1-13.

* cited by examiner

*Primary Examiner* — Alex Liew

(57) ABSTRACT

A method for generating an electronic dental chart for a patient, executed at least in part by a host processor, obtains image data for each of a number of teeth of the patient and generates a template dental chart for the patient that represents the position of each imaged tooth with a symbol according to the obtained image data. The template dental chart for each imaged tooth symbol is populated to form the electronic dental chart by associating the obtained image data to the corresponding symbol in the template dental chart for the imaged tooth, analyzing the obtained image data to identify a condition of the imaged tooth, associating at least the identified condition with the symbol for the imaged tooth, and displaying the populated electronic dental chart, wherein the displayed electronic dental chart provides a visual indication of the identified condition.

17 Claims, 9 Drawing Sheets

AUTOMATIC TOOTH CHARTING USING DIGITAL IMAGES

FIELD OF THE INVENTION

The invention relates generally to the field of diagnostic imaging and more particularly relates to a method and apparatus that automate the task of tooth charting in dental practice.

BACKGROUND OF THE INVENTION

Dental charts aid the dental practitioner in the systematic diagnosis, tracking, and treatment of teeth and supporting structures. Conventional dental charting is a largely manual process, performed by the dental practitioner with the help of a standardized paper template that allows written annotation related to each tooth to be recorded and stored in the patient's file.

With the increased use of electronic tools for image storage and display, the value of maintaining dental charts as digital data that can be displayed as needed is widely recognized. Various types of dental charting software have been developed, such as the SOFTDENT software from Kodak Dental Systems by Carestream Health.

Refer to U.S. Pat. No. 7,010,153 entitled "Tooth Identification Digital X-Ray Images and Assignment of Information to Digital X-Ray Images" (Zimmerman).

Refer to U.S. Patent Application Publication No. 2006/0285636entitled "Dental Image Charting System and Method"(Razzano).

Applicants have recognized that there is a need for automatic tooth charting methods and apparatus that can generate an appropriate dental chart for a particular patient from dental images and populate the generated chart with information obtained from applying automated diagnostics to the tooth image data.

SUMMARY OF THE INVENTION

An object of the present invention is to provide a method for automatic generation of an electronic dental chart for a patient, using information obtained from analysis of any of a number of types of digital images obtained from the patient.

Another object of the present invention is to provide a method for updating an existing electronic dental chart when new data is available from patient images or from measurements obtained from the patient.

Among its advantages, the present invention facilitates generation and update of dental records using data available from image analysis.

Another advantage relates to the capability to present the same dental chart information in a conventional two-dimensional (2-D) format or in a three-dimensional (3-D) format.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for generation of an electronic dental chart for a patient, executed at least in part by a host processor, the method comprising: obtaining image data for each of a plurality of teeth of the patient; generating a template dental chart for the patient that represents the position of each imaged tooth with a symbol according to the obtained image data; populating the template dental chart for each imaged tooth symbol to form the electronic dental chart by: (i) associating the obtained image data to the corresponding symbol in the template dental chart for the imaged tooth; (ii) analyzing the obtained image data to identify a condition of the imaged tooth; (iii) associating at least the identified condition with the symbol for the imaged tooth; and displaying the populated electronic dental chart, wherein the displayed electronic dental chart provides a visual indication of the identified condition.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
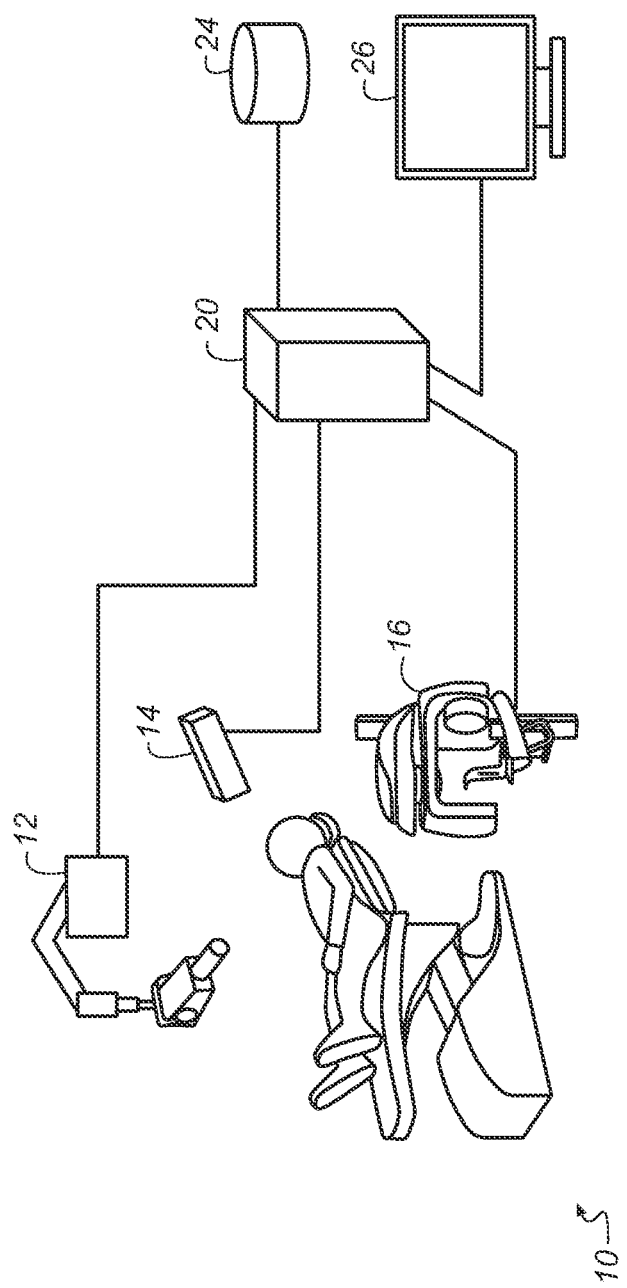
FIG. 1 is a schematic diagram showing a dental information system that generates an electronic dental chart.

The following is a detailed description of the preferred embodiments of the invention, reference being made to the drawings in which the same reference numerals identify the same elements of structure in each of the several figures.

In the drawings and text that follow, like components are designated with like reference numerals, and similar descriptions concerning components and arrangement or interaction of components already described are omitted. Where they are used, the terms "first", "second", and so on, do not necessarily denote any ordinal or priority relation, but may simply be used to more clearly distinguish one element from another.

FIG. 1 shows a dental information system 10 for obtaining patient images and generating an electronic dental chart according to an embodiment of the present invention. Dental information system 10 includes at least one imaging apparatus, which may be an x-ray imaging apparatus 12, a digital camera 14 such as an intra-oral camera, or a dental cone-beam computed tomography (CBCT) system 16 for generating volume images of tooth structure. Other types of imaging apparatus could also be employed for obtaining images of teeth and supporting structures, gums, and related tissue, such as apparatus using ultrasound or other imaging type. In addition, various types of diagnostic measurement instrumentation may also be provided for working with dental information system 10, as described in more detail subsequently.

Still referring to FIG. 1, a host processor 20, such as a computer or other type of dedicated logic processor for obtaining, processing, and storing image data from the imaging apparatus is also part of dental information system 10, along with one or more displays 26 for viewing image results. Host processor 20 is in data communication with one or more image capture devices and, optionally, with any number of automated measurement devices. In addition, host processor 20 can also be in data communication with a database of patient records, stored internally or on a networked host or server, for example A computer-accessible memory 24 is also provided, which may be a non-volatile memory storage device used for longer term storage, such as a device using magnetic, optical, or other data storage media. In addition, computer-accessible memory 24 can comprise a volatile electronic memory such as a random access memory (RAM) within or otherwise in data communication with host processor 20, that is used for shorter term data storage, such as memory used in conjunction with a display device for temporarily storing image content as a display buffer, or memory that is employed to store a computer program having instructions for controlling one or more computers to practice the method according to the present invention.

Figure 2:
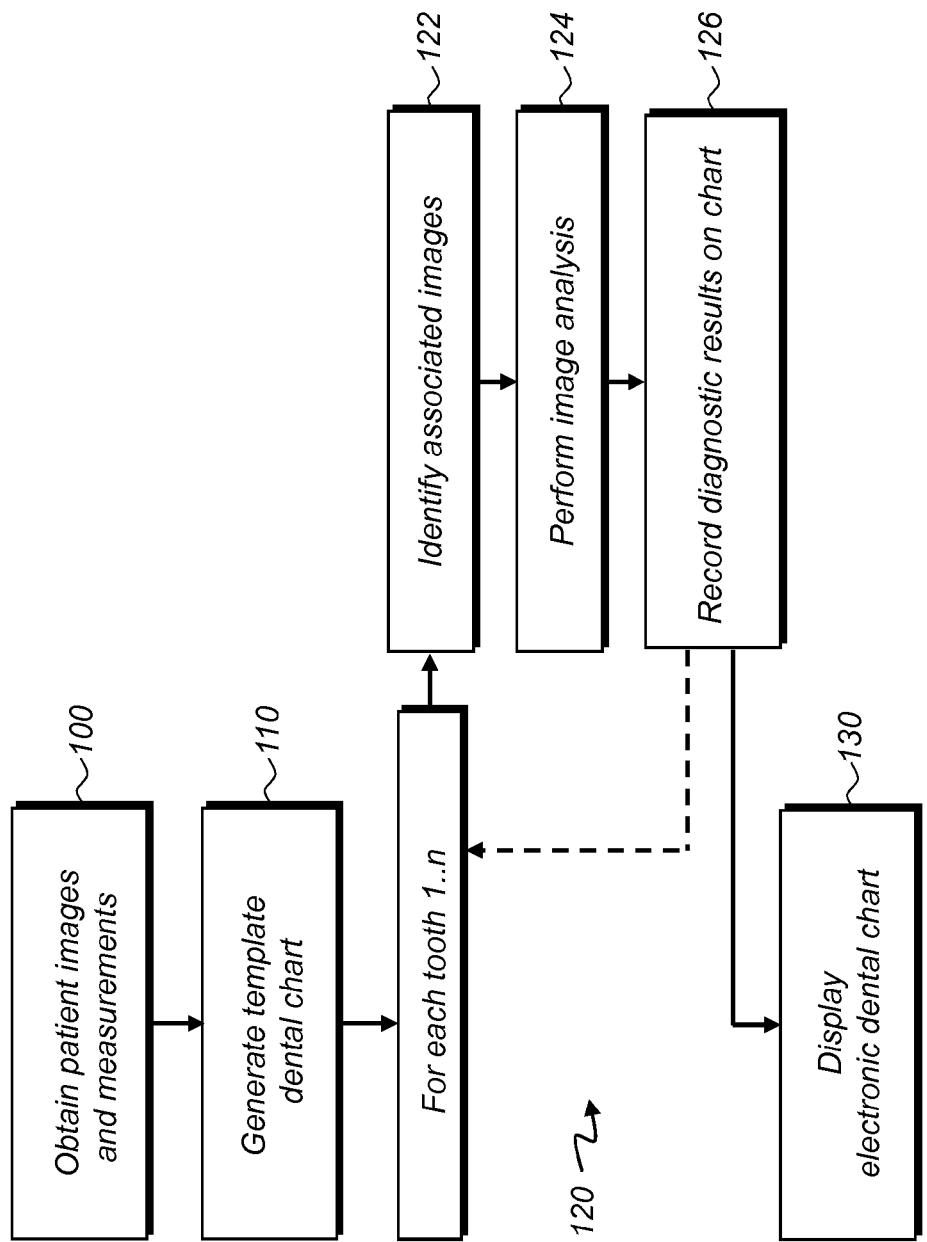
FIG. 2 is a logic flow diagram that shows a process sequence for generating and displaying an electronic dental chart for one or more teeth.
Figure 3A:
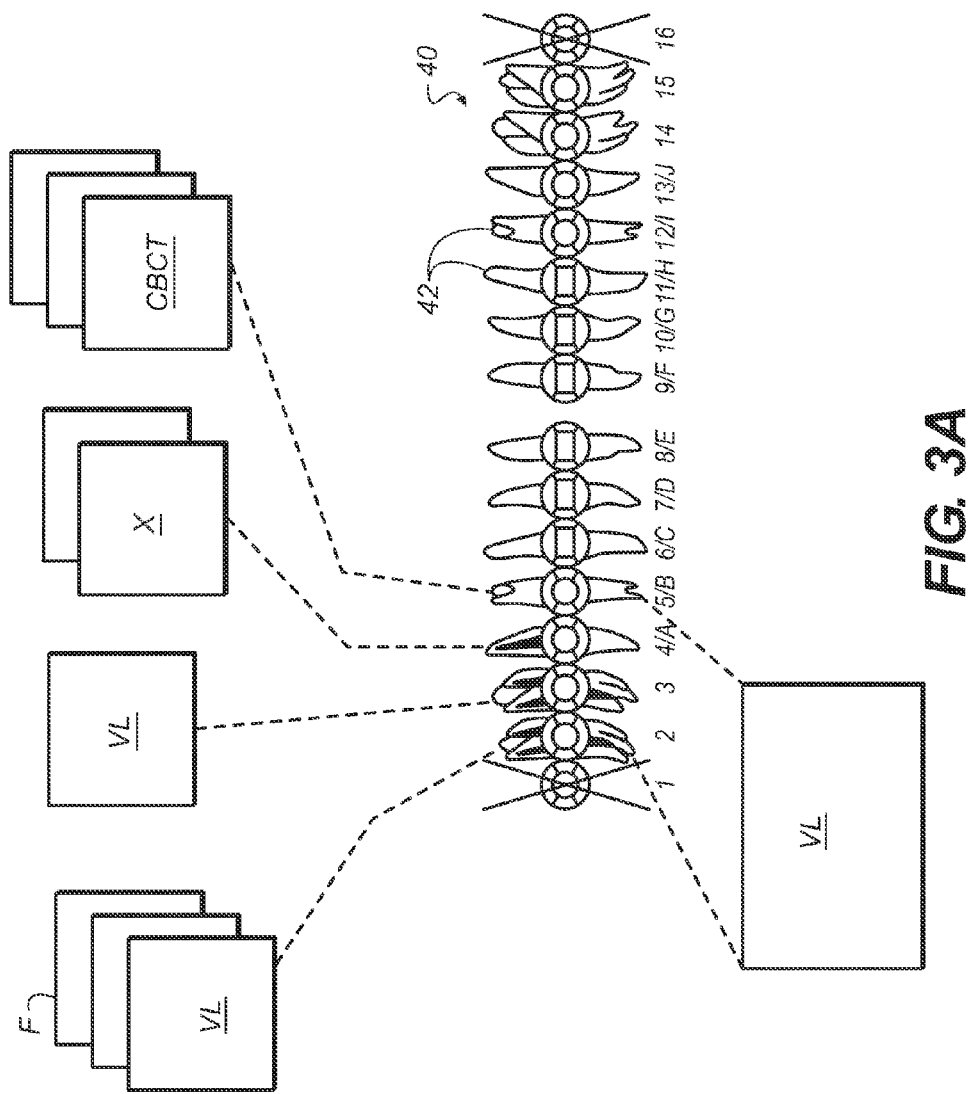
FIG. 3A is a diagram that shows image data related to each of a number of teeth in an electronic dental chart.
Figure 3B:
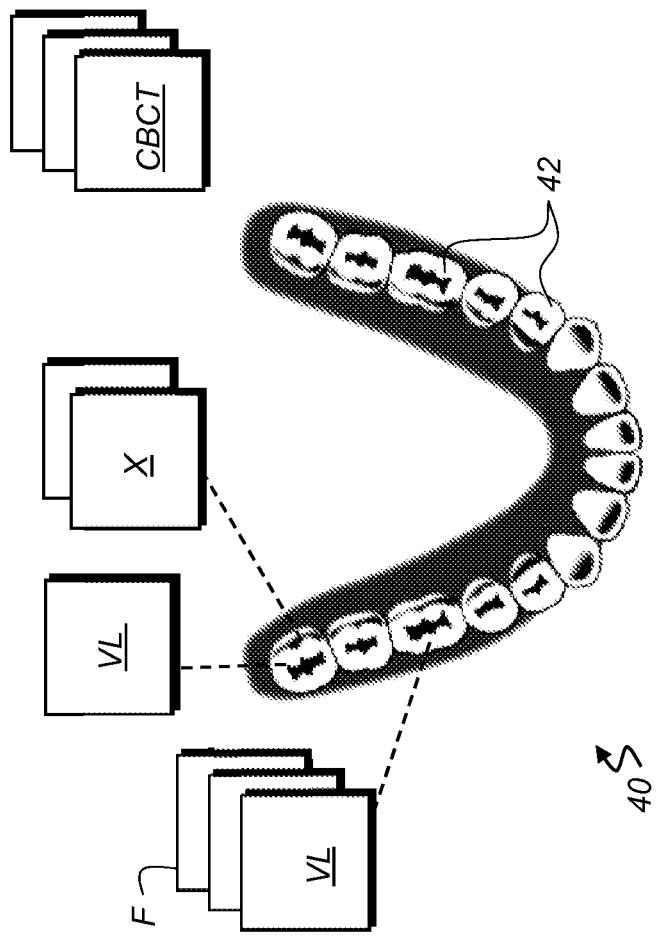
FIG. 3B is a top view diagram that shows image data related to each of a number of teeth in an electronic dental chart according to an alternate embodiment.

The logic flow diagram of FIG. 2 shows a sequence of process steps for generating and displaying an electronic dental chart according to one embodiment of the present invention. FIGS. 3A and 3B represent data structures that are formed in various steps of the FIG. 2 sequence according to one embodiment. In brief, this sequence first obtains and uses a set of multiple images to form a template dental chart 40 for the patient as shown in FIG. 3A. Template dental chart 40 shows, in outline or thumbnail form, the arrangement of teeth that have been detected from obtained images. In this way, template dental chart 40 is analogous to a "blank" standard dental chart that is used as a starting point for recording data for a new patient. There is a symbol 42 for each imaged tooth in template dental chart 40. Unlike a standard printed blank dental chart, however, template dental chart 40 is generated from images of the patient's teeth in one embodiment, using analysis of the images, and shows features that are particular to the patient, such as number of teeth, relative tooth size, and detected tooth outline and angle, as well as overall tooth condition, tooth color, and restorations and other treatments for the tooth or for specific surfaces of the tooth. A standardized template using conventional tooth outline symbols can alternately be used, such as with symbols 42 appropriately highlighted or otherwise marked to indicate whether or not images have been obtained for the corresponding teeth.

Referring to the logic flow shown in FIG. 2, one or more images needed for generating template dental chart 40 are obtained in an obtain images step 100. The images obtained can be any of a number of types of images, as well as combinations that include different types of images. It can be appreciated that, for this processing, at least some amount of image data content is required for a particular tooth in order for that tooth to be presented in template dental chart 40.

As is shown by example for a partial template chart in FIG. 3A and in the alternate top view of FIG. 3B, the images that are obtained can be of one or more image types or modalities, including visible light images (VL), fluorescence images (F), x-ray images (X), image projections used for forming a volume image in CBCT processing, contour images, and ultrasound images. Images obtained directly on digital detectors as well as images from scanned film or storage phosphor media can be used in this way, each image indexed to the symbol 42 for the corresponding tooth. In one embodiment, visible light images are obtained using an intra-oral digital camera. A scanning sequence is carefully followed, beginning in one quadrant of the mouth and progressing along the teeth, obtaining a series of images that will be used for diagnostic purposes, with the information that has been obtained from the teeth used to populate the electronic dental chart. For at least one tooth, multiple images are acquired, such as images taken from different views, for example. These can alternately be images of different types, such as both visible light and fluorescence images whose combination can be used to more effectively show a caries condition. The collected images that are stored for an individual tooth may also include images that provide color or shade information. Manual entry of the tooth number or other identifier is used to associate each image with its corresponding tooth and symbol in the template in one embodiment. A typed entry or screen selection is used to enter the tooth number, such as selecting the corresponding symbol with a computer mouse or other pointer. Alternately, voice recognition can be used for tooth number identification.

In a template generation step 110 (FIG. 2), the obtained images are identified by the tooth number entered by the technician or are correlated to individual teeth in the patient's mouth in some other way, such as by following a set sequence of image capture steps prompted by the system, by automatic recognition in which images are analyzed and correlated to the appropriate tooth automatically, by explicit technician labeling, or by some other means. In one embodiment, previously stored images can be accessed from a local or remote memory and each image associated with its corresponding symbol 42 in template dental chart 40. Tooth outline and related features from the obtained images are then used to generate the arrangement of symbols 42 in template dental chart 40 for the patient. Multiple template dental charts 40 can be generated for the same patient, such as using different views of the set of teeth with different symbols 42, for example, as shown in the side view of FIG. 3A and the top view of FIG. 3B. Alternately, a single template could be used, with a single symbol 42 for storing and accessing one or more images for each tooth. In one embodiment, a combination of templates is employed, each linked to other template views, allowing the practitioner to navigate from one template view to another by entering an instruction on the display or on a control console, for example. This provides different presentations of the patient's mouth, allowing local positioning of symbols to indicate which portion of a tooth has a restoration, for example.

In addition to use of 2-D images, a 3-D image, such as a reconstructed CBCT image, can be used as a basis for generating at least some portion of template dental chart 40. Alternately, a 3-D contour image, obtained by projecting, recording, and analyzing a contour pattern or projection fringe pattern from the tooth surface, could be used for generating template dental chart 40. In one embodiment, a 3-D template is provided as an alternative type of dental chart image. This can be advantageous for storing images appropriately and for accessing image data for each successive tooth.

In one embodiment, template dental chart 40 is generated directly from the image data. The chart that is generated contains symbols for only those teeth for which images have been obtained. Thus, the dental chart for a particular patient may appear to be incomplete, including only those teeth having images accessible to the system. A reduced-size image, or an outline image generated from other images of a particular tooth, is used to represent the tooth as symbol 42 in template dental chart 40, rather than using a standard tooth outline pattern. Where a tooth has been extracted or is missing, there can be a corresponding blank spot or a specific symbol indicating a removed or missing tooth in template dental chart 40.

Still referring to the sequence of FIG. 2, a template population step 120 then populates the template dental chart for a set of one or more teeth by analyzing the obtained image data to identify a condition, such as caries, a restoration, or a treatment for one or more teeth in the set. In the example process shown in FIG. 3A, template population step 120 loops successively through each tooth, identifies images related to the tooth in an identify images step 122, performs image analysis in an image analysis step 124, and records results in a recording step 126, associating a condition detected in image analysis step 124 with the corresponding tooth. The tooth condition may include detected caries as well as previous restorations or treatments, and may include a condition that is not visible, such as a root canal or implant, for example.

Image analysis step 124 in the FIG. 2 sequence can utilize any of a number of computer-aided diagnostic tools that are available for determining a tooth condition, including not only caries or other detected problem, but also restoration or previous treatment data. One example of an available diagnostic technique is the fluorescence imaging with reflectance enhancement (FIRE) technique taught in commonly-assigned U.S. Pat. No. 7,596,253 entitled "Method And Apparatus For Detection Of Caries" to Wong et al., incorporated herein by reference. FIRE imaging enhancement combines both fluorescence and reflectance effects for caries detection. FIRE imaging techniques can also be used to identify crowns and fillings of various types, as well as to distinguish one type of filling from another. Automatic identification of various types of restorations can then be entered directly into the electronic dental chart for the patient. Operator or practitioner verification may or may not be requested for such automated entry.

In addition to FIRE imaging, other tools that can be used include visible light techniques, fluorescent light detection techniques, and automated analysis of x-ray images. Automated analysis of data from visible, fluorescent, or x-ray image data, or from some combination of image data from any number of image data sources, can be used for detection of caries and other conditions. Image processing algorithms can also detect various types of treatment applied to teeth, including sealant, implant, crown, bridge, fillings and various filling types, or other conditions. Any automatically detected condition data are stored and associated with each tooth or group of teeth. Various types of codes and symbols can be used to represent tooth conditions or treatments, automatically entered and updated as new image data for the patient is obtained.

In addition to diagnostic data, color shade data, such as visual color values that are associated with some portion of the tooth, can be stored. These can be values from a standard color space, such as hue-saturation-brightness value (HSV) or Commission Internationale de L'Éclairage L*a*b* (CIELAB) color space, for example.

Alternately, image analysis step 124 can use practitioner observations, allowing annotation for entering text comments on tooth condition as well as symbols to indicate conditions or treatment that may not have been identified automatically.

Information from panoramic x-ray image data can also be used with dental chart 40. Panoramic images can provide information on hidden features such as root canal treatment and implants. Image thresholding can be used to detect the presence of metal and other materials in the x-ray image. In addition, panoramic images can also be analyzed for tooth identification, such as by shape identification or other suitable processing, enabling a panoramic image to be automatically processed for entry of data on hidden features for one or more teeth.

Figure 3C:
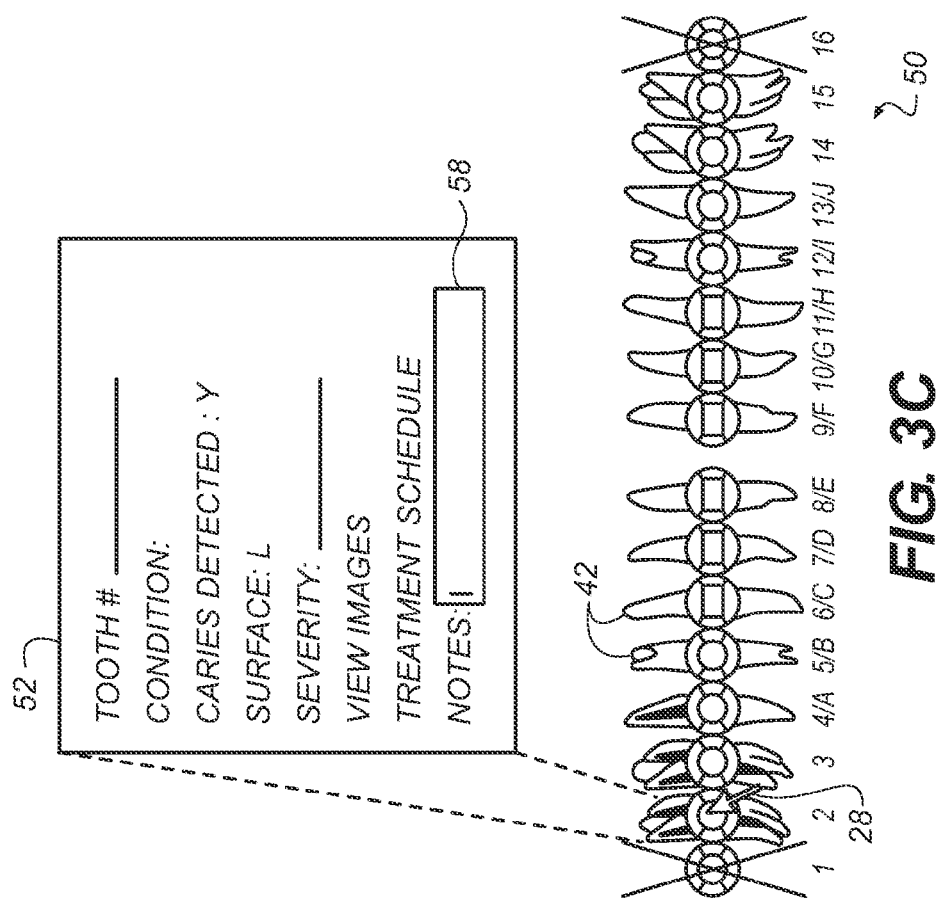
FIG. 3C is a diagram that shows some of the reference data that is available for a tooth in an electronic dental chart according to one embodiment.

Following recording step 126 (FIG. 2), the results of automated image analysis are available with each of one or more teeth. As is shown in FIG. 3C, these results can be accessed and displayed from a populated electronic dental chart 50 in a display step 130. In the example of FIG. 3C, "hovering" or placing a mouse cursor 28 or using some other pointing element to a designated tooth symbol 42 in the displayed electronic dental chart 50 enables the display of the corresponding diagnostic results generated for the tooth using the process outlined in FIG. 2. A window 52 (FIG. 3C) shows results for a specified tooth in one embodiment. This may be a pop-up window or, alternately, a dedicated area of a user interface screen for display of stored information on any selected tooth. The system provides a visual indication of any identified condition. In one embodiment, the symbol for a selected tooth is enlarged or highlighted and different views of any selected tooth are available, such as views achieved by rotating the tooth to enable information on which portion of the tooth has been restored, for example.

It can be appreciated that further information can alternately be added, based on practitioner observations or on measured data, including data not associated with a particular image. The dental practitioner may want to enter additional data relevant to a tooth in electronic dental chart 50, such as by typed or audible entry. Alternately, scanned notes or other data could also be provided and linked with electronic dental chart 50.

As is shown in FIG. 3C, window 52 includes an optional "Notes" text field 58 for practitioner annotation of the displayed data. This also enables the practitioner to edit and correct information about the tooth that has been automatically generated.

Figure 4A:
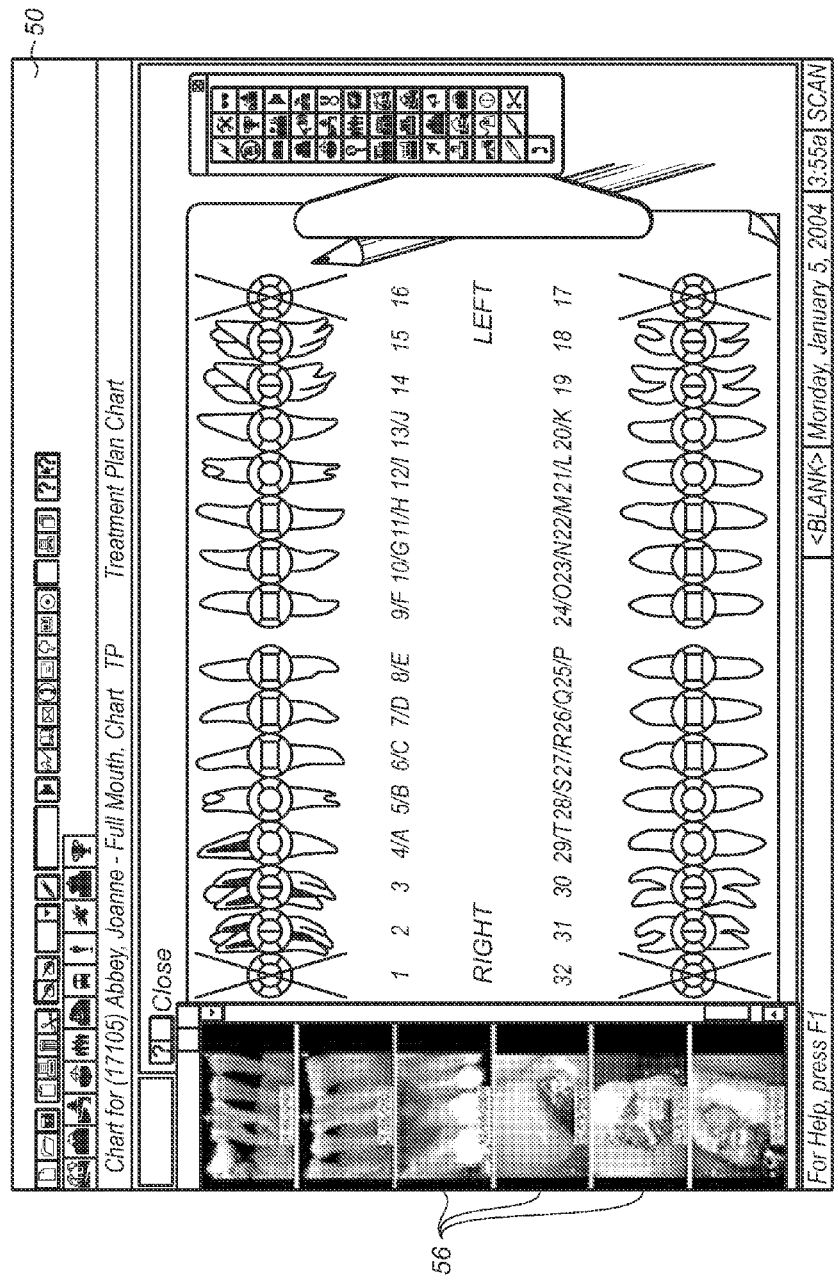
FIG. 4A is a user interface example showing an electronic dental chart.

In one embodiment, a link is generated between at least one tooth in the electronic dental chart 50 and the obtained image data that is stored for the at least one tooth, such as stored on a different host processor or stored in a networked database, for example. In the electronic dental chart, tooth images display as index images 56 in reduced size or "thumbnail" form, such as along the side of displayed electronic dental chart 50, as shown in FIG. 4A. An image can be enlarged on the display when the corresponding index image 56 is selected by the practitioner. In one embodiment, index images 56 scroll vertically as a computer mouse or other pointer is moved across the electronic dental chart 50 display. Various codes and color-coding can be used as a visual indication to indicate an identified condition of each tooth, using standardized or customized notation. For example, a red color could be used to indicate a tooth requiring near-term treatment. Other colors could be used to indicate teeth needing particular attention or monitoring or to indicate portions of teeth having a particular type of restoration. At least a portion of this coding and notation is initially generated by computer-automated detection/diagnostics software. In one embodiment, color highlighting or indexing is used to indicate what types of images are available for each tooth.

Figure 4B:
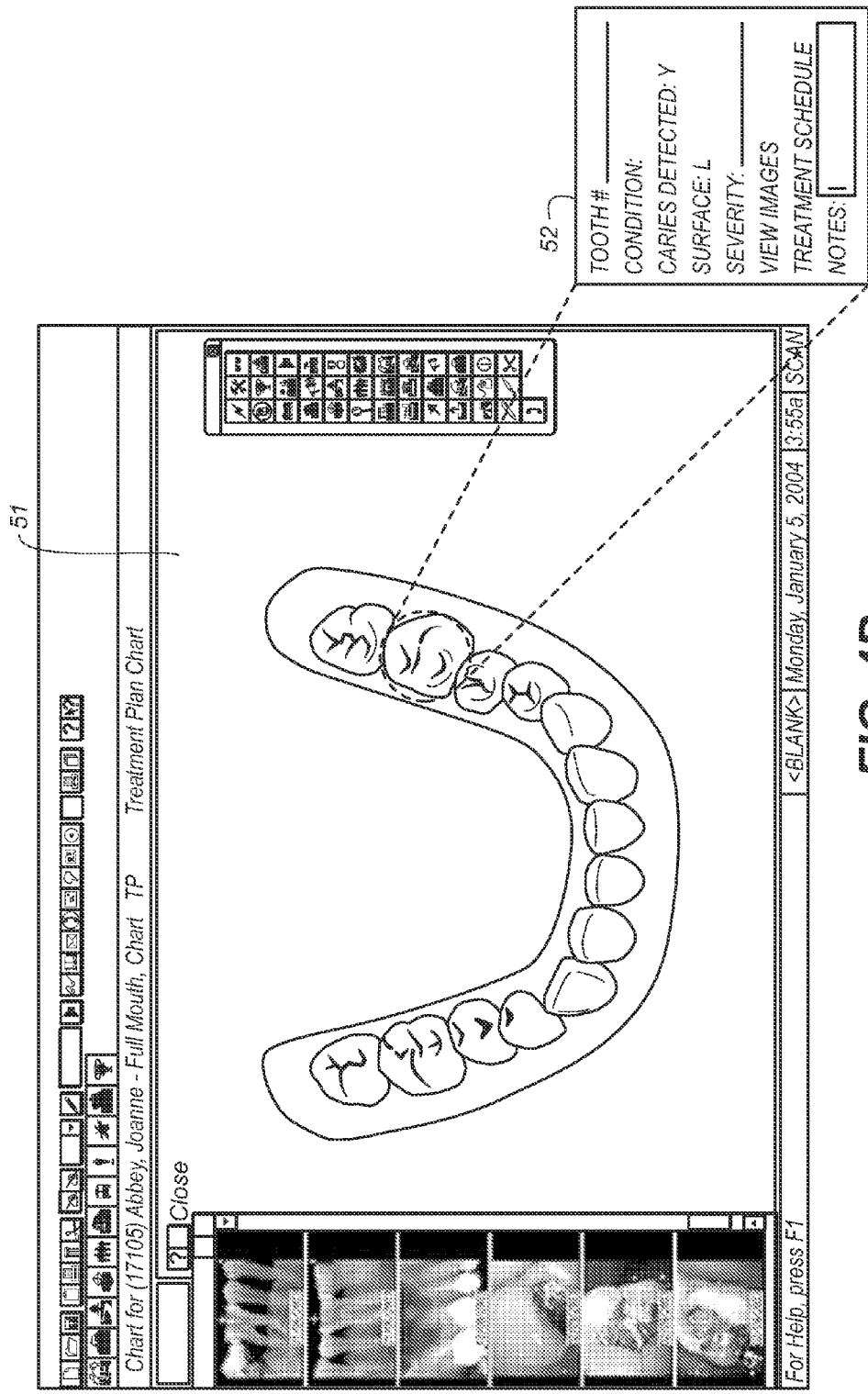
FIG. 4B is a user interface example showing an alternate electronic dental chart with a 3-D representation of the patient's teeth.
Figure 5:
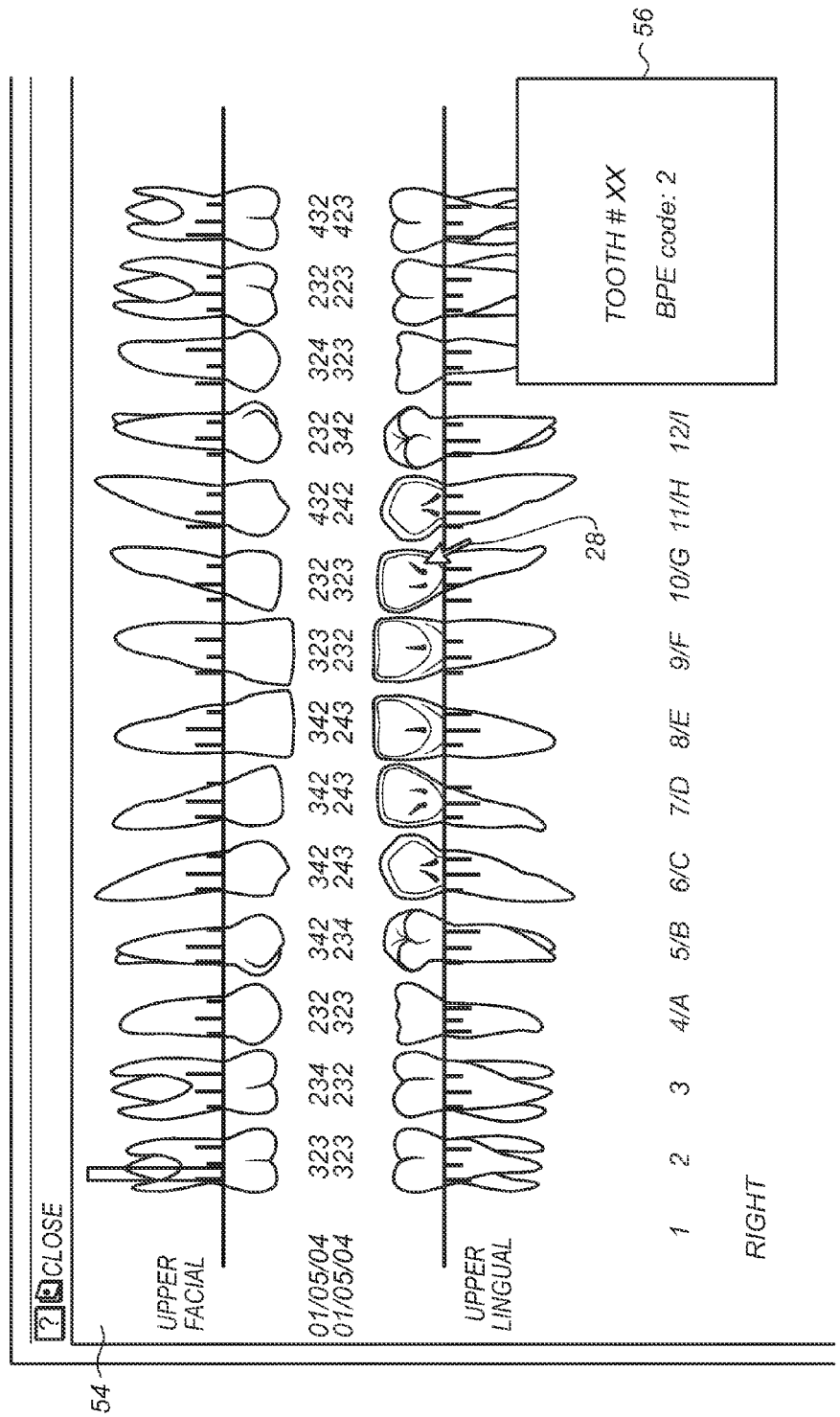
FIG. 5 is an example of a chart that provides additional measurement information.

Embodiments of the present invention further expand upon the conventional 2-D dental chart to provide dental charting with alternative 3-D views where these views are available from CBCT imaging, from contour imaging, or from some other 3-D imaging type. Referring to FIG. 4B, there is shown, by way of example, an alternate 3-D view of a dental chart 51 that can be presented instead of, or as an alternative to, the more conventional 2-D dental chart 50 provided in FIG. 4A for some portion or all of the patient's teeth. In one embodiment, the viewer can switch between 2-D and 3-D viewing modes for dental chart 50 or 51 using a user interface command. This allows the system to present the same dental chart information in both a conventional 2-D format and in a 3-D format, according to viewer preference, where 3-D information is available. In one embodiment, the 3-D representation can be rotated or oriented to a position that is favorable for viewing or for access to corresponding stored images.

In one embodiment, the 3-D information displays using a standard template. In another embodiment, the 3-D display is derived from contour imaging, CBCT imaging, or other 3-D imaging of the patient.

In addition to information obtained from digital images of the tooth, measurement information can also be obtained and recorded to support electronic dental chart 50. A practitioner command displays a measurement chart 54 that records periodontal probe measurements and entry of BPE (Basic Periodontal Examination) codes that give pocket depth values for surfaces near the teeth. Manual or automated entry of periodontal measurements can be obtained for display on chart 54. In one embodiment, an automated probe is provided for generating measurement data. A number of types of automated probes are available for measuring periodontal pocket depth, including probes using ultrasonic, optical, or mechanical measurement devices. These devices generate a digital signal that provides the periodontal measurement data. In another embodiment, an audio transcription device records the manual reading obtained by the dental practitioner, obtaining the measurement data in a "hands-free" mode of operation. Manual entry of BPE codes or other related values is another option. One advantage in using the display for this purpose is that periodontal measurement data can be displayed graphically, enabling the practitioner to identify problems or areas of concern at a glance and to monitor troublespots more effectively. In addition, the periodontal measurements can be accessed in conjunction with information specific to a tooth. As with tooth information obtained from image content, cursor 28 can be used to point to a tooth or area and display useful measurement information, such as in a window 56, for example.

Figure 6:
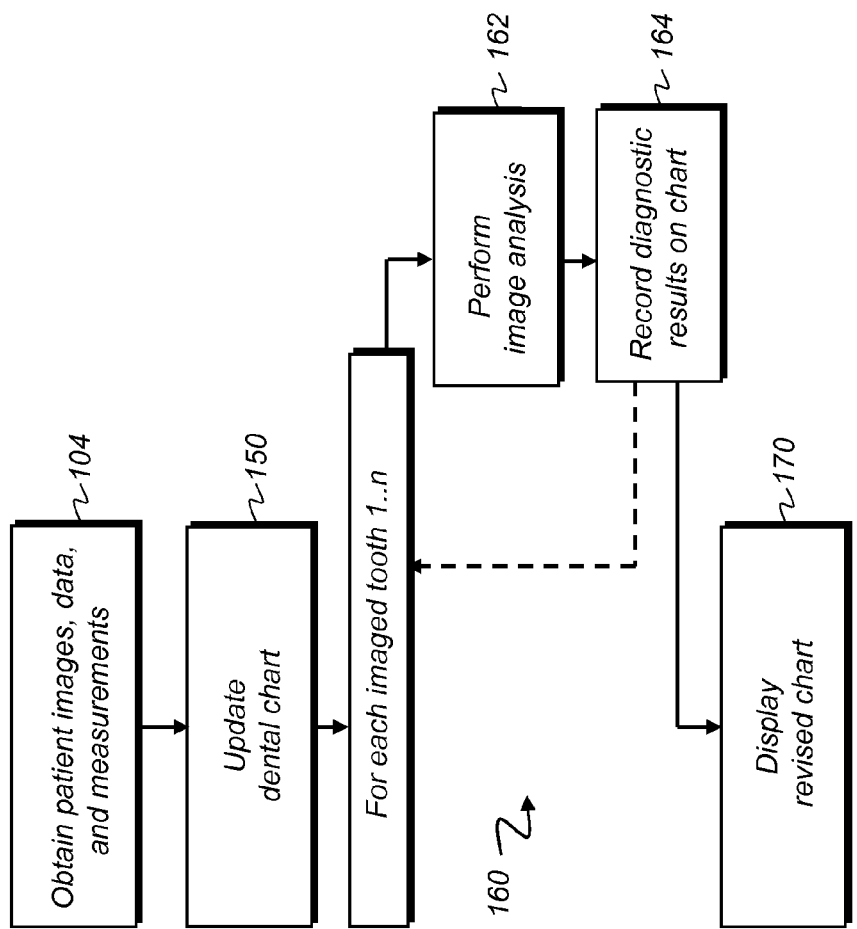
FIG. 6 is a logic flow diagram that shows a process sequence for updating an existing electronic dental chart.

Once electronic dental chart 50 has been generated, it can be used to support and improve treatment work flow. Electronic dental chart 50 acts as a tool for recording subsequent information and updates on tooth condition or treatment and can serve as a guide for generation of a treatment plan for the patient. The logic flow diagram of FIG. 6 shows a sequence of steps for update of the electronic dental chart. An obtain images, data, and measurements step 104 enables the practitioner to update images of the patient's teeth of any type and to correlate these with the existing electronic dental chart 50. Images used can include any of the types of images that were used initially to generate electronic dental chart 50. Additional information about the tooth or about tooth treatment, such as a recent restoration, can be automatically or manually entered. In one embodiment, control software prompts the dentist or dental technician to obtain an image or to provide any information about teeth for which there is currently no available image or other data. An update step 150 then uses this additional information to generate a revised electronic dental chart 50. A template population step 160 sequences through each tooth for which additional images and information have been made available. For each tooth, an image analysis step 162 is executed and results stored in a recording step 164. A display step 170 then displays the revised electronic dental chart, updated with the new information.

Among features available using the electronic dental chart are links to timing and scheduling software and utilities. For example, a practitioner can enter a command to send a reminder to obtain X-rays of an area of interest upon the next patient visit or after a given time interval. This information could be used as a feed to the scheduling software that is used at the dental facility.

It can be seen that the electronic dental chart of the present invention acts not only as an electronic version of the conventional paper dental chart, but also provides a convenient tool for storage of updated information on a patient's intraoral condition and, for some aspects of diagnosis and treatment, can help to guide and organize collection of subsequent data on the patient's teeth and overall oral health. The electronic dental chart can cooperate with automated tools that provide images, measurement, and analysis for obtaining dental data. As new diagnostic utilities are developed, for example, the electronic dental chart can be reconfigured to incorporate their capabilities as support utilities, helping the dental practitioner to more effectively treat patient conditions. As another advantage, fairly complete dental information about a patient can be broadcast from one site to another. This can help the patient to get the proper dental care when out of town or after moving to a new location that is not served by a particular dental practice.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for generating an electronic dental chart for a patient, executed at least in part by a processor, comprising:
    obtaining image data for each of a plurality of teeth of the patient;
    generating a template dental chart for the patient representing the position of each of the plurality of teeth with a symbol according to the obtained image data, wherein the template dental chart is representative of one or more features of each of the plurality of teeth obtained from the image data;
    populating the template dental chart for each symbol to form the electronic dental chart by, for each of the plurality of teeth:
        (i) associating the obtained image data to the corresponding symbol in the template dental chart for the tooth;
        (ii) analyzing the obtained image data to identify a condition of the tooth; and
        (iii) associating the identified condition with the symbol for the tooth; and
    displaying the populated electronic dental chart, wherein the displayed electronic dental chart provides a visual indication of the identified condition.

2. The method of claim 1 wherein obtaining image data comprises obtaining image data from one or more of a digital camera, an x-ray system, a cone-beam computed tomography system, and an ultrasound system.

3. The method of claim 1 wherein the identified condition is taken from the group consisting of caries, a filling, a filling type, a crown, sealing, a root canal, and an implant.

4. The method of claim 1 wherein displaying the electronic dental chart further comprises displaying images associated with at least one of the plurality of teeth according to the position of a pointer on the displayed electronic dental chart.

5. The method of claim 1 further comprising annotating entries on the electronic dental chart according to information provided by a dental practitioner about at least one of the plurality of teeth.

6. The method of claim 1 wherein populating the template dental chart further comprises obtaining and storing periodontal measurement data that relates to the electronic dental chart.

7. The method of claim 6 wherein the periodontal measurement data is obtained from a digital signal.

8. The method of claim 1 further comprising recording an instruction to schedule image acquisition during a subsequent patient visit.

9. The method of claim 1 wherein generating the template dental chart comprises processing an image for the tooth to obtain an outline image.

10. The method of claim 1 wherein generating the template dental chart comprises generating a three-dimensional dental image.

11. The method of claim 1 further comprising storing one or more values that represent a color shade for the at least one tooth.

12. The method of claim 1 further comprising updating the electronic dental chart for the patient for one or more teeth by:
　obtaining digital image data for at least one image for at least one tooth of the patient;
　analyzing the at least one obtained image to identify a condition of the imaged tooth;
　associating at least the identified condition with the symbol for the imaged tooth in the electronic dental chart to form an updated dental chart; and
　displaying the updated electronic dental chart.

13. The method of claim 1 wherein populating the template dental chart is performed, at least in part, by an automated procedure.

14. The method of claim 1 further comprising indicating the position of one or more missing teeth on the template dental chart.

15. The method of claim 1 wherein the obtained image data is a panoramic x-ray image.

16. A method for displaying dental images for a patient, the method comprising:
　obtaining digital image data for each of a plurality of teeth of the patient;
　generating a template dental chart for the patient that represents the position of each of the plurality of teeth with a symbol that is generated from the obtained image data, wherein the template dental chart is representative of one or more features of each of the plurality of teeth obtained from the digital image data;
　populating the template dental chart for each of the plurality of teeth to form an electronic dental chart that relates the obtained image data to the corresponding symbol for each of the plurality of teeth; and
　displaying the electronic dental chart and displaying, along with the electronic dental chart, one or more index images related to symbols on the electronic dental chart according to viewer selection.

17. The method of claim 16 wherein displaying the electronic dental chart comprises displaying either a three-dimensional dental chart or a two-dimensional dental chart in response to an instruction.

* * * * *